(12) United States Patent
Kim et al.

(10) Patent No.: US 10,933,237 B2
(45) Date of Patent: Mar. 2, 2021

(54) SYSTEM, METHOD, AND COMPUTER PROGRAM FOR PROVIDING TRAINING FOR PAIN IMPROVEMENT

(71) Applicant: NUNAPS INC., Seoul (KR)

(72) Inventors: Dong Ho Kim, Seoul (KR); Dong Wha Kang, Seoul (KR)

(73) Assignee: NUNAPS INC., Seoul (KR)

( * ) Notice: Subject to any disclaimer, the term of this patent is extended or adjusted under 35 U.S.C. 154(b) by 0 days.

(21) Appl. No.: 16/741,959

(22) Filed: Jan. 14, 2020

(65) Prior Publication Data

US 2020/0147380 A1 May 14, 2020

Related U.S. Application Data

(63) Continuation of application No. PCT/KR2018/007947, filed on Jul. 13, 2018.

(30) Foreign Application Priority Data

Jul. 14, 2017 (KR) .................. 10-2017-0089868

(51) Int. Cl.
*A61B 5/00* (2006.01)
*A61F 7/00* (2006.01)
(Continued)

(52) U.S. Cl.
CPC ........ *A61N 1/36021* (2013.01); *A61B 5/0006* (2013.01); *A61B 5/0008* (2013.01);
(Continued)

(58) Field of Classification Search
CPC combination set(s) only.
See application file for complete search history.

(56) References Cited

U.S. PATENT DOCUMENTS

| 4,653,507 A | 3/1987 | Laudadio |
| 5,191,896 A * | 3/1993 | Gafni .................. A61B 5/4824 600/555 |

(Continued)

FOREIGN PATENT DOCUMENTS

| KR | 10-2010-0025373 A | 3/2010 |
| WO | 2005/039688 A2 | 5/2005 |

(Continued)

OTHER PUBLICATIONS

Levitt, H. (1971). Transformed up-down methods in psychoacoustics. Journal of the Acoustical Society of America,49, 467-477 (Year: 1971).*

(Continued)

*Primary Examiner* — Joseph A Stoklosa
*Assistant Examiner* — Adam J Avigan
(74) *Attorney, Agent, or Firm* — Studebaker & Brackett PC

(57) ABSTRACT

The inventive concept refers to a system, a method, and a computer program for providing training for pain improvement. According to an exemplary embodiment, a training providing method for pain improvement includes requesting, by a computer, a temperature providing device to provide a first temperature to a first body point, requesting, by the computer, the temperature providing device to provide a second temperature to a second body point, requesting a user to select a temperature matched with a specific condition among the first temperature and the second temperature, and calculating a correct answer rate after performing a trial of distinguishing between the first temperature and the second temperature by a predetermined number.

10 Claims, 7 Drawing Sheets

(51) Int. Cl.
*A61B 5/0484* (2006.01)
*A61N 1/36* (2006.01)
(52) U.S. Cl.
CPC ............ *A61B 5/483* (2013.01); *A61B 5/0484* (2013.01); *A61F 7/007* (2013.01); *A61F 2007/0086* (2013.01); *A61F 2007/0093* (2013.01)

(56) References Cited

U.S. PATENT DOCUMENTS

| | | | |
|---|---|---|---|
| 6,018,675 | A | 1/2000 | Apkarian et al. |
| 2006/0089551 | A1 | 4/2006 | England |
| 2007/0010860 | A1* | 1/2007 | Gafni ............... A61B 5/0484 607/96 |
| 2009/0099623 | A1* | 4/2009 | Bentwich ............. A61N 5/0613 607/45 |
| 2009/0270757 | A1 | 10/2009 | Backonja |

FOREIGN PATENT DOCUMENTS

| | | |
|---|---|---|
| WO | 2006/100638 A1 | 9/2006 |
| WO | 2015/063221 A1 | 5/2015 |

OTHER PUBLICATIONS

Levy D, Abraham R, Reid G. A comparison of two methods for measuring thermal thresholds in diabetic neuropathy. J Neurol Neurosurg Psychiatry. 1989;52(9):1072-1077. doi:10.1136/jnnp.52.9.1072 (Year: 1989).*

Jamal et al. (1985). An Improved Automated Method for the Measurement of Thermal Thresholds. Journal of Neurology, Neurosurgery, and Psychiatry. 48: 354-360. (Year: 1985).*

Bertelsmann et al. Thermal discrimination thresholds in normal subjects and in patients with diabetic neuropathy. J Neurol Neurosurg Psychiatry. Jul. 1985;48(7):686-90 (Year: 1985).*

International Search Report issued in PCT/KR2018/007947; dated Jul. 13, 2018.

The extended European search report issued by the European Patent Office dated Jun. 17, 2020, which corresponds to European Patent Application No. 18831448.8-1115 and is related to U.S. Appl. No. 16/741,959.

* cited by examiner

SYSTEM, METHOD, AND COMPUTER PROGRAM FOR PROVIDING TRAINING FOR PAIN IMPROVEMENT

CROSS-REFERENCE TO RELATED APPLICATIONS

The present application is a continuation of International Patent Application No. PCT/KR2018/007947, filed on Jul. 13, 2018 which is based upon and claims the benefit of priority to Korean Patent Application No. 10-2017-0089868 filed on Jul. 14, 2017. The disclosures of the above-listed applications are hereby incorporated by reference herein in their entirety.

BACKGROUND

Embodiments of the inventive concept described herein relate to a system, a method, and a computer program for providing training for pain improvement, and more particularly, relate to a system, a method, and a computer program for providing training for relieving or eliminating chronic pain.

Pain stimulus is usually caused by partial damage to tissue adjacent to a specific nerve fiber. This is called acute pain. This change in tissue causes chemicals for activating the nociceptive fibers in the skin to be secreted and to act at nerve endings; the chemicals include neuropeptides, serotonin, histamine, and the like. The action potential generated in the neurons by the combination of the chemicals is connected to the spinal cord's dorsal horn and synapses in the spinal cord and stimulates the pain fibers to secrete glutamate and material P. Accordingly, information about pain may be transmitted to the brain's thalamus.

However, even when there is no damage to body tissues and the stimulus of the normal threshold or more is not applied to the body tissues, there are patients (e.g., chronic pain patients, patients with complex pain syndrome, or the like) who have no stimulus or who feel pain even at low stimulus due to brain abnormalities.

The medication treatment (the treatment with narcotic or nonnarcotics), acupuncture treatment, local electrical stimulation treatment, and surgical treatment are used as the conventional method of treating chronic pain. However, this treatment method has several side effects for patients. Accordingly, there is a need for the invention that treats chronic pain by training patient's brain without causing side effects in the patient.

SUMMARY

Embodiments of the inventive concept provide a system, a method, and a computer program for providing training for the pain improvement that relieves or eliminates chronic pain by providing the patient with the training for distinguishing first temperature and second temperature, which are different each other, to increase pain threshold.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a training providing method for pain improvement includes requesting, by a computer, a temperature providing device to provide a first temperature to a first body point, requesting, by the computer, the temperature providing device to provide a second temperature to a second body point, requesting a user to select a temperature matched with a specific condition among the first temperature and the second temperature, and calculating a correct answer rate after performing a trial of distinguishing between the first temperature and the second temperature by a predetermined number.

Furthermore, in another embodiment, when the correct answer rate is not greater than a reference condition, the method further includes repeatedly providing the training for distinguishing between the first temperature and the second temperature under the same condition.

Moreover, the method further includes adjusting the first temperature and the second temperature based on the correct answer rate.

According to an exemplary embodiment, a training providing method for pain improvement includes requesting, by a computer, a temperature providing device to provide a first temperature to a first body point, requesting, by the computer, the temperature providing device to provide a second temperature to a second body point, requesting a user to select a temperature matched with a specific condition among the first temperature and the second temperature, and calculating a correct answer rate by performing pain improvement training. The pain improvement training is to perform the specific number of trials for distinguishing the first temperature and the second temperature. The method further includes calculating the correct answer rate and adjusting the first temperature and the second temperature based on the correct answer rate.

Also, in another embodiment, the method further includes making a request for providing the first temperature and the second temperature to the first body point and the second body point at the same time.

Furthermore, in another embodiment, the method further includes setting the first body point and the second body point to the same body point to sequentially provide the first temperature and the second temperature while changing an order of the first temperature and the second temperature for each training trial.

Moreover, in another embodiment, the first temperature is set to the same temperature as an expected threshold temperature or a temperature lower than the expected threshold temperature by a specific value, and the second temperature is set to a temperature with a high reference temperature interval from the first temperature.

Also, in another embodiment, the method further includes adjusting the expected threshold temperature by a reference interval after performing training of the specific number and determining an evaluation threshold temperature based on the correct answer rate at each expected threshold temperature.

Furthermore, in another embodiment, the adjusting of the temperature further includes adjusting the reference temperature interval based on the expected threshold temperature.

Moreover, in another embodiment, the method further includes receiving brain image data obtained by capturing the user's brain during the training trial and calculating the evaluation threshold temperature through the analysis of the brain image data.

Also, in another embodiment, the method further includes setting, by the computer, reference image data. The reference image data is generated by the computer or is generated by an external server, based on brain image data upon performing pain training of a normal person and is received.

Furthermore, in another embodiment, the temperature providing device links with the computer through wired or wireless communication to receive at least one of a first temperature value, a second temperature value, an provision order of the first temperature and the second temperature, and the number of trials.

Moreover, in another embodiment, the temperature providing device includes three or more temperature transmitters providing different temperatures; the adjusting of the temperature includes making, by the computer, a request for changing the first temperature transmitter or the second temperature transmitter to a third temperature transmitter providing a third temperature when a first temperature transmitter provides the first temperature and a second temperature transmitter provides the second temperature.

According to an exemplary embodiment, a training providing computer program for pain improvement is coupled to a computer being hardware to perform the above-described training providing method for pain improvement and is stored in media.

According to an exemplary embodiment, a training providing system for pain improvement includes a control device performing the above-described training providing method for pain improvement and a temperature providing device configured to providing different temperatures simultaneously or continuously. The temperature providing device links with the control device through wired or wireless communication so as to be controlled by the control device.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
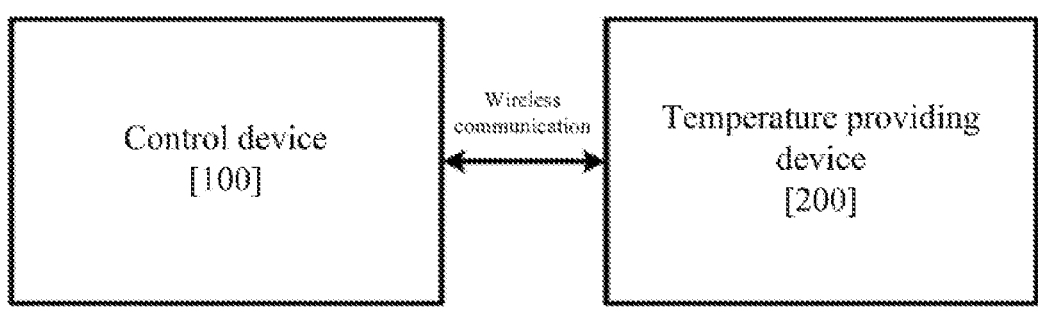
FIG. 1 is a connection relationship diagram of a training providing system for pain improvement, according to an embodiment of the inventive concept.

Hereinafter, exemplary embodiments of the inventive concept will be described in detail with reference to the accompanying drawings. The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

A 'computer' includes all various devices capable of providing results to a user by performing arithmetic processing. For example, the computer may correspond to not only a desktop personal computer (PC) or a notebook but also a smart phone, a tablet PC, a cellular phone, a personal communication service phone (PCS phone), a mobile terminal of a synchronous/asynchronous International Mobile Telecommunication-2000 (IMT-2000), a palm PC, a personal digital assistant (PDA), and the like. Furthermore, the computer may correspond to a server that receives a request from a client and then performs information processing.

In this specification, 'pain improvement training' refers to the training that increases the pain threshold for pain improvement. For example, the 'pain improvement training' refers to the training for the specific number of trials to select a temperature (e.g., high temperature or low temperature) that satisfies a specific condition among first and second temperatures different from each other.

In this specification, 'expected threshold temperature' refers to the temperature estimated as the threshold temperature by the computer to set the first temperature or the second temperature.

In this specification, 'evaluation threshold temperature' refers to the temperature determined as a user's actual pain threshold.

In this specification, 'reference temperature interval' refers to the value applied as the difference value between the first temperature and the second temperature, as the temperature difference at which the user is capable of detecting the temperature difference.

Hereinafter, according to embodiments of the inventive concept, a system, a method, and a computer program for providing training for pain improvement will be described in detail with reference to the drawings.

FIG. 1 is a connection relationship diagram of a training providing system for pain improvement, according to an embodiment of the inventive concept. Referring to FIG. 1, according to an embodiment of the inventive concept, the training providing system for pain improvement includes a control device 100 and a temperature providing device 200.

The control device 100 is a device that provides a pain improvement training model. That is, the control device 100 sets the temperature condition, temperature provision order, or the like to the temperature providing device 200. The control device 100 may be a computer (e.g., a smartphone, or the like) in which a program providing a training method for pain improvement to be described later is installed and may be a separately manufactured device that provides a training method for pain improvement to be described later. Accordingly, the control device 100 may be referred to as a "computer".

The temperature providing device 200 is a device that provides different temperatures simultaneously or continuously. The temperature providing device 200 communicates with the control device 100 by wire or wirelessly so as to be controlled by the control device 100. For example, the temperature providing device 200 communicates with the control device 100 by wire or wirelessly, and thus at least one of the first temperature value and the second temperature value, the order of providing the first temperature and the second temperature, and the number of trials may be controlled. According to an embodiment, when the temperature providing device 200 is made of a wearable device capable of being worn on the body, the temperature providing device 200 may be connected to the control device 100 (e.g., a mobile terminal such as a smartphone) through wireless communication (e.g., Bluetooth communication, or the like). As the temperature providing device 200 is made of a wearable device, a patient may often perform training for pain improvement while easily wearing the temperature providing device 200. The temperature providing device 200 may include various devices capable of providing different temperatures to the body point under control of the control device 100.

Figure 2:
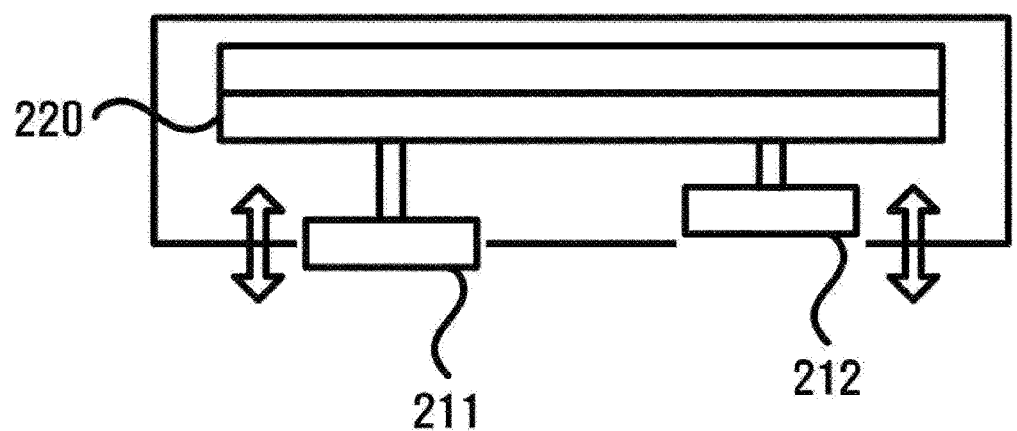
FIGS. 2 to 3B illustrate exemplary view of a temperature providing device in a training providing system, according to embodiments of the inventive concept.

As illustrated in FIG. 2, the temperature providing device 200 may include a temperature control module 220 capable of controlling temperature. For example, the temperature control module 220 may be a module for heating or cooling a fluid filled in a device. In this case, the temperature control module 220 may repeatedly provide the first temperature and the second temperature to the body point, by repeatedly heating and cooling the fluid. Furthermore, the temperature providing device 200 may further include a plurality of temperature transmitters 211 and 212, of which the temperature is controlled by the temperature control module 220; the temperature providing device 200 may contact each of the plurality of temperature transmitters 211 and 212 to one or more body points (e.g., a point on the skin), simultaneously or sequentially.

The temperature providing device 200 includes the first temperature transmitter 211 providing the first temperature and the second temperature transmitter 212 providing the second temperature, which are disposed at different points (points corresponding to the first body point and the second body point). The first temperature transmitter 211 moves to the first body point at the time of providing the first temperature; the second temperature transmitter 212 moves to the second body point at the time of providing the second temperature.

Figure 3A:
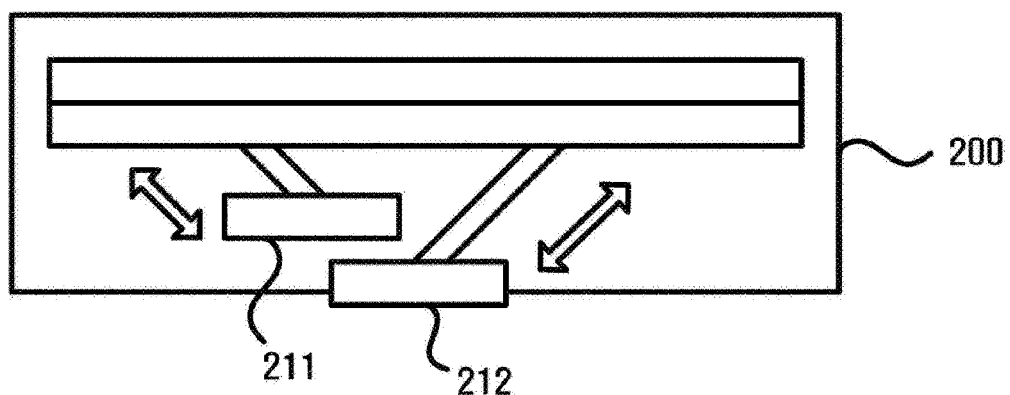

As the modified example, as illustrated in FIG. 3A, the temperature providing device 200 may be manufactured in the form of a wearable device (i.e., a body-mounted device). For example, the temperature providing device 200 is made in the band type; the first temperature transmitter 211 is moved and positioned at the first point of the inner surface in contact with the first body point at the time of providing the first temperature; the second temperature transmitter 212 is moved and positioned at the second point of the inner surface in contact with the second body point at the time of providing the second temperature.

Figure 3B:
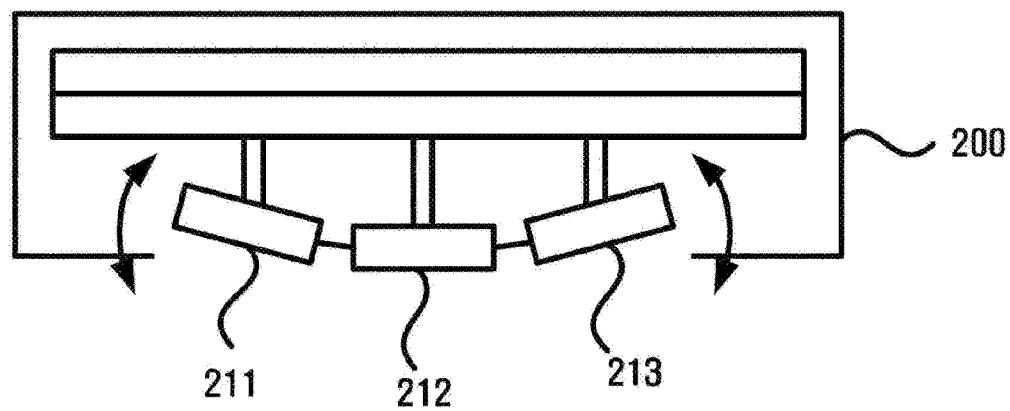

As another modified example, as illustrated in FIG. 3B, the temperature providing device 200 may have the form in which the plurality of temperature transmitters 211, 212, and 213 are connected to one or more motors (not illustrated). In this case, at least one of the plurality of temperature transmitters 211, 212, and 213 may move to one or more body points depending on the driving of the motor (e.g., rotational driving).

In the meantime, the plurality of temperature transmitters 211, 212, and 213 may have various forms. For example, each of the plurality of temperature transmitters 211, 212, and 213 may be a heat transfer plate of which the temperature is controlled by electricity and may be formed of a tube through which a fluid having a specific temperature flows. When the plurality of temperature transmitters 211, 212, and 213 are heat transfer plates, the temperature control module 220 may be a module that supplies power to generate heat to the plurality of temperature transmitters 211, 212, and 213.

Figure 4:
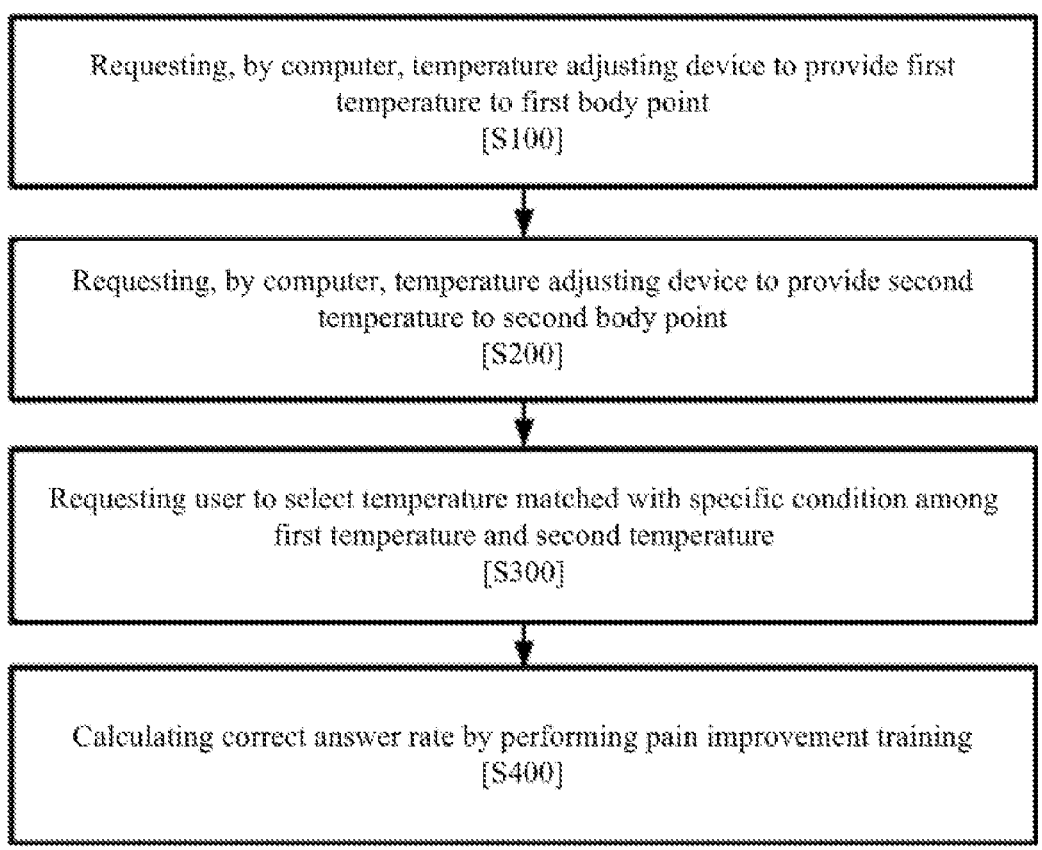
FIGS. 4 to 8 are flowcharts of a training providing method for pain improvement, according to embodiments of the inventive concept.

FIG. 4 is a flowchart of a training providing method for pain improvement, according to an embodiment of the inventive concept. As illustrated in FIG. 4, according to an embodiment, the training providing method for pain improvement includes an operation S100 of requesting, by the control device 100, the temperature adjusting device 200 to provide first temperature to the first body point; an operation S200 of requesting, by the control device 100, the temperature adjusting device 200 to provide second temperature to the second body point, an operation S300 of requesting a user to select temperature matched with a specific condition, among the first temperature and the second temperature, and an operation S400 (calculating a correct answer rate) of calculating a correct answer rate by performing pain improvement training.

Hereinafter, the operation S100 of requesting, by the control device 100, the temperature adjusting device 200 to provide the first temperature to the first body point and the operation S200 of requesting, by the control device 100, the temperature adjusting device 200 to provide the second temperature to the second body point will be described. Various methods may be applied to the method in which the control device 100 requests the temperature adjusting device 200 to provide the first temperature and the second temperature.

According to an embodiment, as illustrated in FIG. 2, the control device 100 requests the temperature adjusting device 200 to provide the first and second temperatures to the first and second body points, simultaneously or sequentially. At this time, the first and second body points are the body points (e.g., the first and second points of the skin) of a specific user (i.e., patient or trainee), for example, the first and second points of the skin.

For example, when the temperature adjusting device 200 is a bracelet-type device in contact with the skin of a cuff, the first temperature transmitter 211 and the second temperature transmitter 212 are placed to be opposite to each other at different points of the skin of the cuff and are simultaneously or sequentially in contact (positioned) with the first body point and the second body point to provide the first temperature and the second temperature. In this case, the first temperature transmitter 211 may provide the first temperature to the first body point; the second temperature transmitter 212 may provide the second temperature to the second body point.

Moreover, according to another embodiment, as illustrated in FIGS. 3A and 3B, the control device 100 sets the first body point and the second body point to the same body point and repeatedly requests the temperature providing device 200 to provide the first and second temperatures to the same body point by changing the order in which the first and second temperatures are provided for each training trial. That is, the control device 100 requests the temperature adjusting device 200 to perform a plurality of trials performed while the temperature adjusting device 200 changes the order of providing the first temperature transmitter 211 and the second temperature transmitter 212 to the specified single body point.

Moreover, various methods may be applied to a method of setting the first temperature and the second temperature.

According to an embodiment, the control device 100 determines the expected threshold temperature expected as the threshold, and sets the first and second temperatures based on the expected threshold temperature. As a specific example, the control device 100 sets the first temperature to a temperature the same as the expected threshold temperature or lower than the expected threshold temperature by a specific value and sets the second temperature to a temperature higher than the first temperature by a reference temperature interval. At this time, the specific value for setting the first temperature refers to a value for setting a temperature lower than the expected threshold temperature to the first temperature while the value approximates the expected threshold temperature, as a value less than the reference temperature interval.

Also, in another specific example, the control device sets the reference temperature (i.e., the expected threshold temperature) to the first temperature, sets the second temperature to a plurality of temperatures higher or lower than the first temperature, and requests the patient to determine which stimulus is higher among the first temperature stimulus and the second temperature stimulus presented to the patient. The order in which the first and second temperatures are presented may be a random order (i.e., the order in which the first and second temperatures are presented in each training trial may not be determined). Furthermore, training difficulty may be increased by reducing the difference between the first temperature and the second temperature.

Hereinafter, the operation S300 of requesting a user to select temperature matched with a specific condition, among the first temperature and the second temperature will be described. For example, the control device 100 may request the user to select high or low temperature between the first temperature and the second temperature. In an embodiment, when the control device 100 provides the first temperature and the second temperature sequentially, the control device 100 provides (e.g., guide a point in time when the first temperature and the second temperature are provided through the method of providing visual information on a screen or providing auditory information) identification information to the user at a point in time when the first temperature and the second temperature are provided, and receives the selection of options corresponding to a specific condition (e.g., a higher one of high temperature or low temperature) from the user.

In another embodiment, when different temperatures (i.e., the first temperature and the second temperature) are provided to different body points by the temperature providing device 200, the control device 100 receives the selection of options corresponding to a specific condition (e.g., higher temperature or lower temperature among the two temperatures) from the user based on the location. For example, in the case of the temperature providing device 200 of the bracelet-type device, the first temperature transmitter 211 and the second temperature transmitter 212 are placed on the left and right sides of the bracelet-type device, respectively, and the control device 100 receives the left side or right side as a correct answer option from the user.

Hereinafter, the operation S400 (calculating a correct answer rate) of calculating a correct answer rate by performing pain improvement training will be described. At this time, the pain improvement training is to perform the specific number of trials for distinguishing the first temperature and the second temperature. The control device 100 calculates the correct answer rate based on the correct answer entered in a plurality of trials. The control device 100 determines whether the user correctly distinguishes the first temperature and the second temperature, through the correct answer rate.

Figure 5:
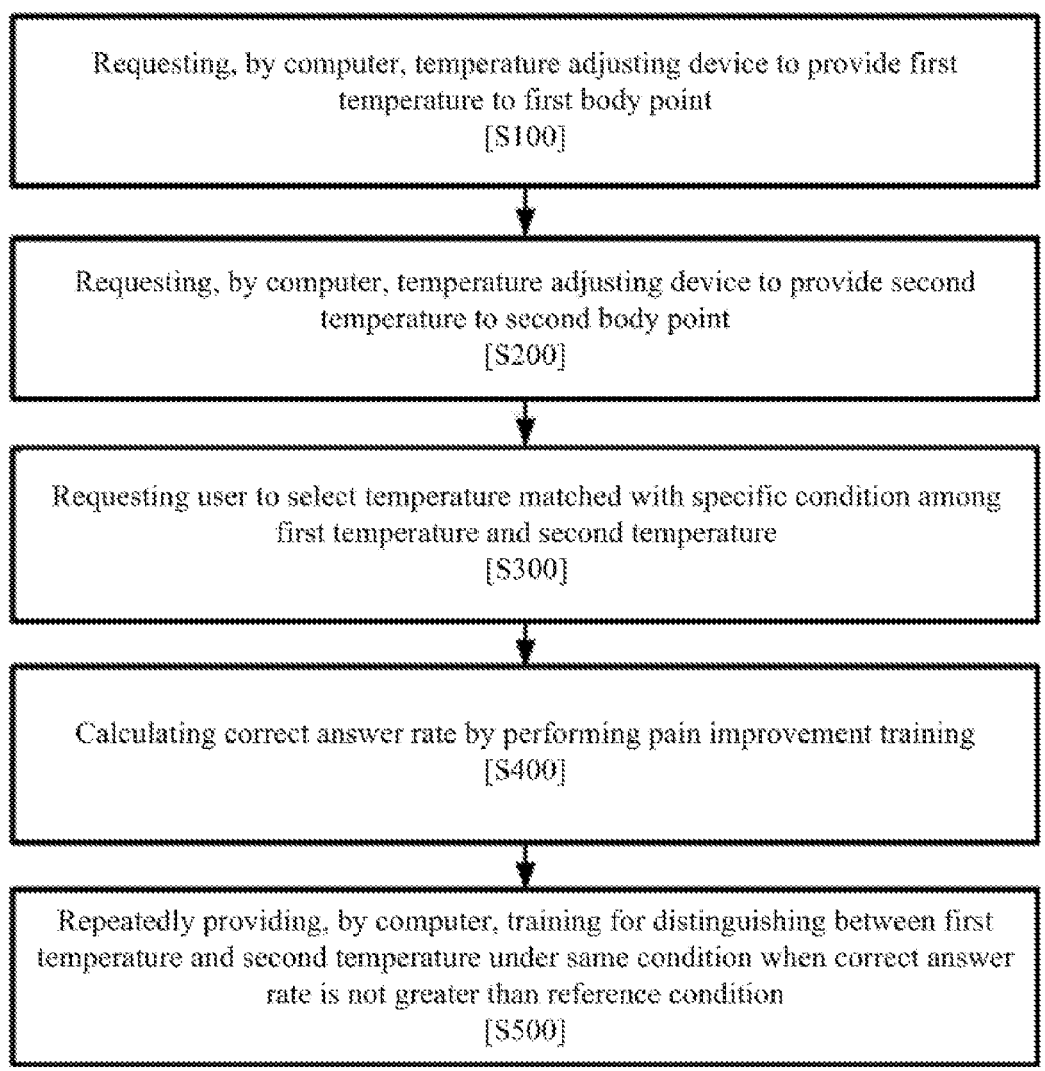

In addition, in another embodiment, as illustrated in FIG. 5, when the correct answer rate is not greater than the reference condition, the control device 100 further includes an operation S500 of repeatedly providing the training for distinguishing between the first temperature and the second temperature under the same condition. When the correct answer rate is not greater than the reference condition, it is determined that the user does not properly distinguish between the first temperature and the second temperature. Accordingly, the control device 100 may repeatedly perform the training by applying the same first temperature and the same second temperature as the previous training.

In this way, the pain threshold may be increased or a new sensory cognitive representation may be generated to distinguish between the first temperature and the second temperature in the user's brain. That is, as the training of distinguishing between the first temperature and the second temperature is repeatedly provided, the threshold of pain may be increased or the new sensory cognitive representation that compensates for pain perception nerve damage caused by brain damage may be generated; thus, as the user does not recognize both the first temperature and the second temperature as the same pain, chronic pain may be reduced or treated by distinguishing between the first temperature and second temperature (i.e., by increasing the pain threshold).

Figure 6:
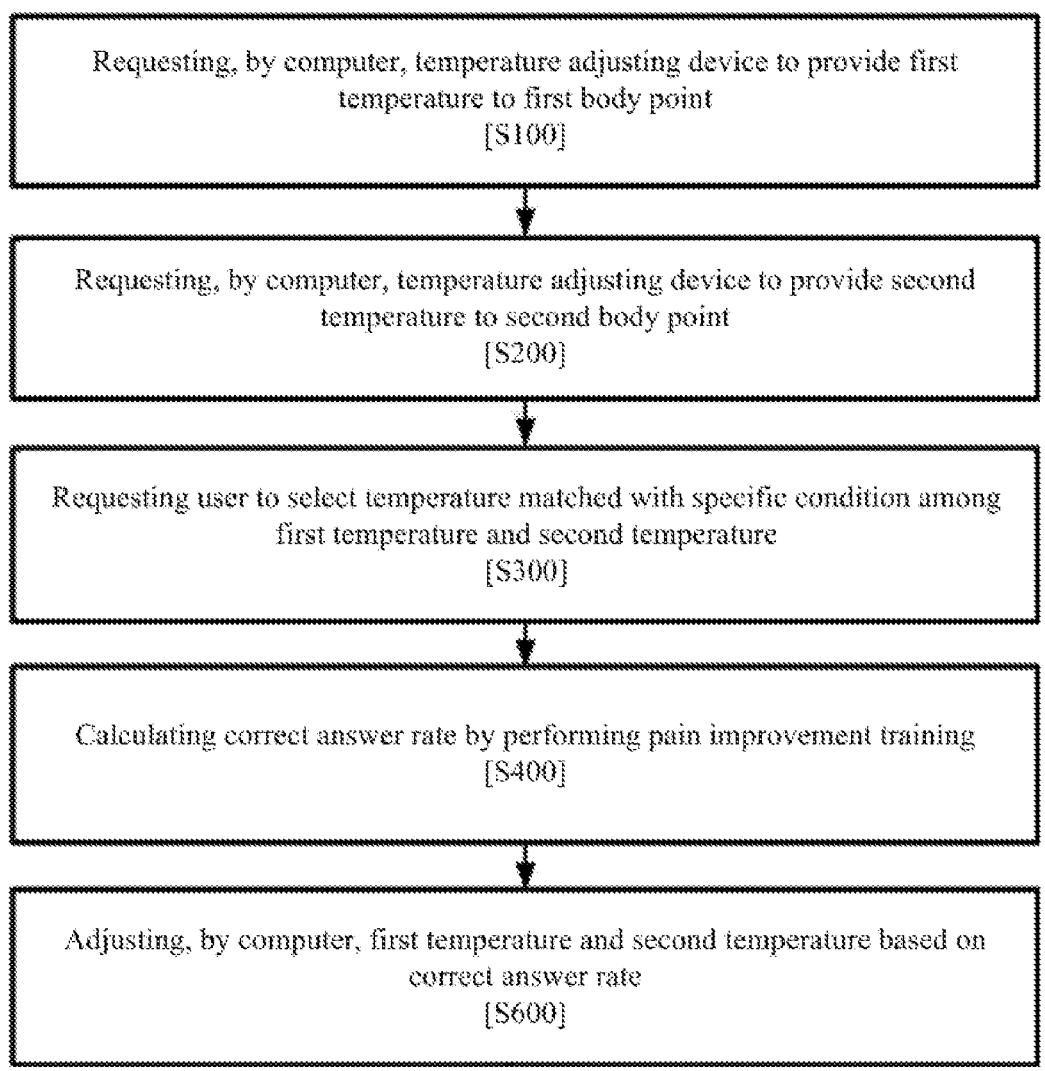

Furthermore, as illustrated in FIG. 6, in another embodiment, the control device 100 further includes an operation S600 of adjusting the first temperature or the second temperature based on the correct answer rate. For example, the control device 100 increases the first temperature and the second temperature to increase the user's pain threshold. When the first temperature and the second temperature are set based on the expected threshold temperature as the reference, the control device 100 adjusts the expected threshold temperature based on the correct answer rate. When the correct answer rate is high, the control device 100 may increase the interval of temperature adjustment (e.g. increase the expected threshold temperature). As the user's ability to distinguish between the first temperature and the second temperature is not improved when the training is performed by providing the first temperature and the second temperature higher than the user's current pain threshold, the user's threshold increase effect may be low, and thus the temperature adjustment is performed by reflecting the correct answer rate when the previous training is performed.

Moreover, an operation S600 of adjusting temperature includes adjusting a reference temperature interval based on the expected threshold temperature. The difficulty of training provided to the patient may be adjusted by adjusting the reference temperature interval corresponding to the difference between the first temperature and the second temperature. For example, the training of distinguishing relatively great temperature difference may be provided patients with severe chronic pain by increasing the reference temperature interval; the training with the high difficulty of temperature discrimination may be provided to patients with mild chronic pain by decreasing the reference temperature interval.

The method in which the control device 100 requests the temperature adjusting device 200 to adjust the temperature value corresponding to the first temperature or the second temperature may vary depending on the type of the temperature adjusting device 200. For example, the temperature adjusting device 200 includes three or more temperature transmitters 211, 212, and 213 providing different temperatures; the first temperature transmitter 211 provides the first temperature; the temperature transmitter 212 provides the second temperature; the third temperature transmitter 210 provides the third temperature; in this case, in the operation S600 of adjusting temperature, the control device 100 make a request for changing the first temperature transmitter 211 or the second temperature transmitter 212 to the third temperature transmitter 213.

Figure 7:
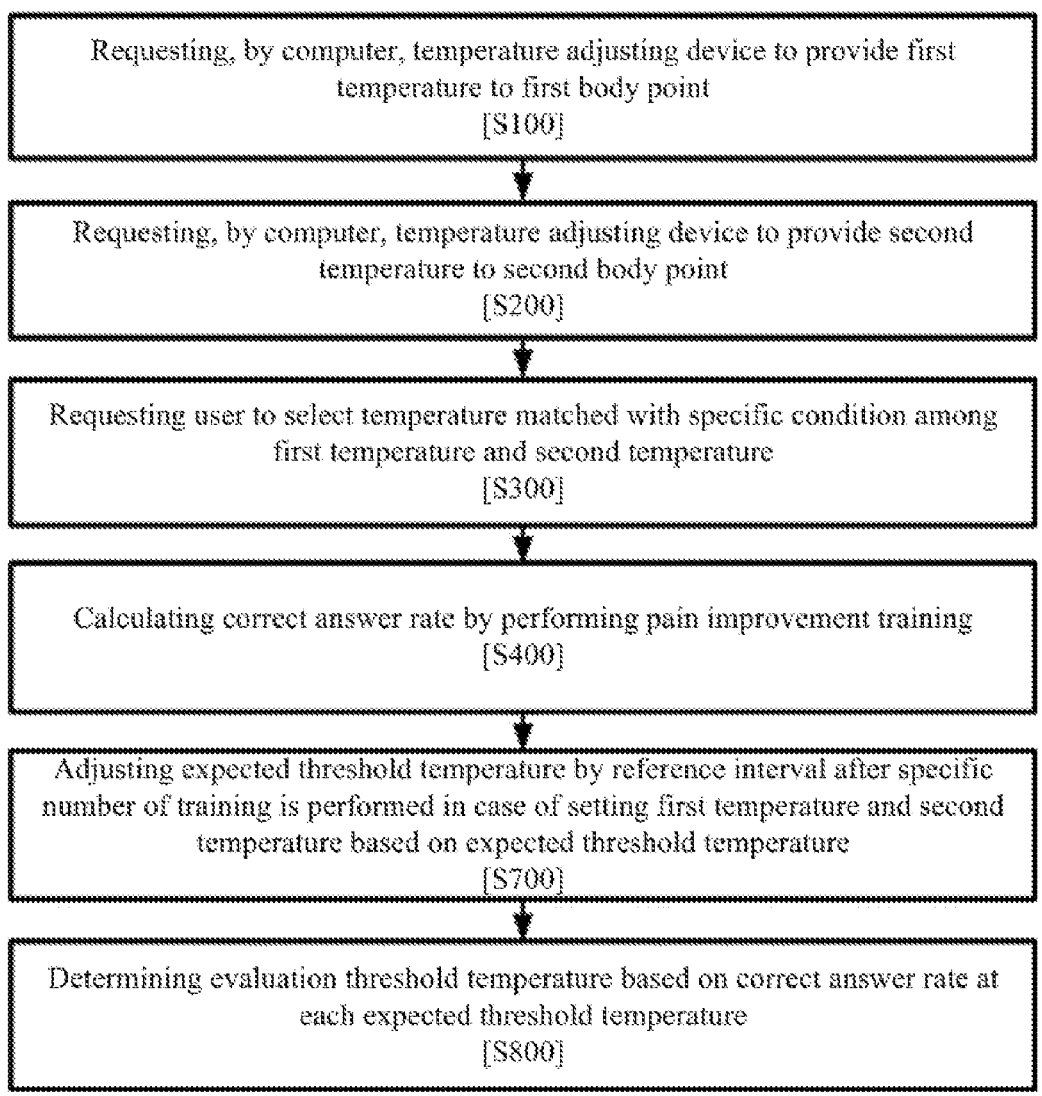

Also, as illustrated in FIG. 7, in another embodiment, in the case of setting the first temperature and the second temperature based on the expected threshold temperature, the method further includes an operation S700 of adjusting the expected threshold temperature by the reference temperature interval after the specific number of training is performed and an operation S800 of determining the evaluation threshold temperature based on the correct answer rate at each expected threshold temperature. The control device 100 calculates the evaluation threshold temperature corresponding to the user's actual pain threshold, based on the result of performing the training on several expected threshold temperatures.

In S700, the control device 100 repeats a procedure of performing the training based on the first temperature and the second temperature that are on the basis of the specific expected threshold temperature and calculating the correct answer rate at each training while the expected threshold temperature is increased by the reference temperature interval. As a result, the control device 100 obtains the correct answer rate for a plurality of expected threshold temperatures.

In S800, the control device 100 calculates the evaluation threshold temperature based on the correct answer rate for each expected threshold temperature. For example, the control device 100 generates the evaluation threshold temperature by generating the graph of a correct answer rate change according to each expected threshold temperature.

Also, in another embodiment, the method may further include determining the second temperature or the expected threshold temperature for performing the next training, using the correct answer rate for each second temperature based on the expected threshold temperature. For example, the control device applies the correct answer rate values for each second temperature presented in the training process to linear or nonlinear session analysis, calculates temperatures at each of which the expected correct answer rate corresponds to 55%, 60%, 70%, 80%, or 90%, and set the calculated temperatures to the value of the second temperature to be used to perform the next training. The temperature interval between the plurality of second temperatures may have a log scale interval, and the interval may be adjusted depending on the correct answer rate of the training performance.

Figure 8:
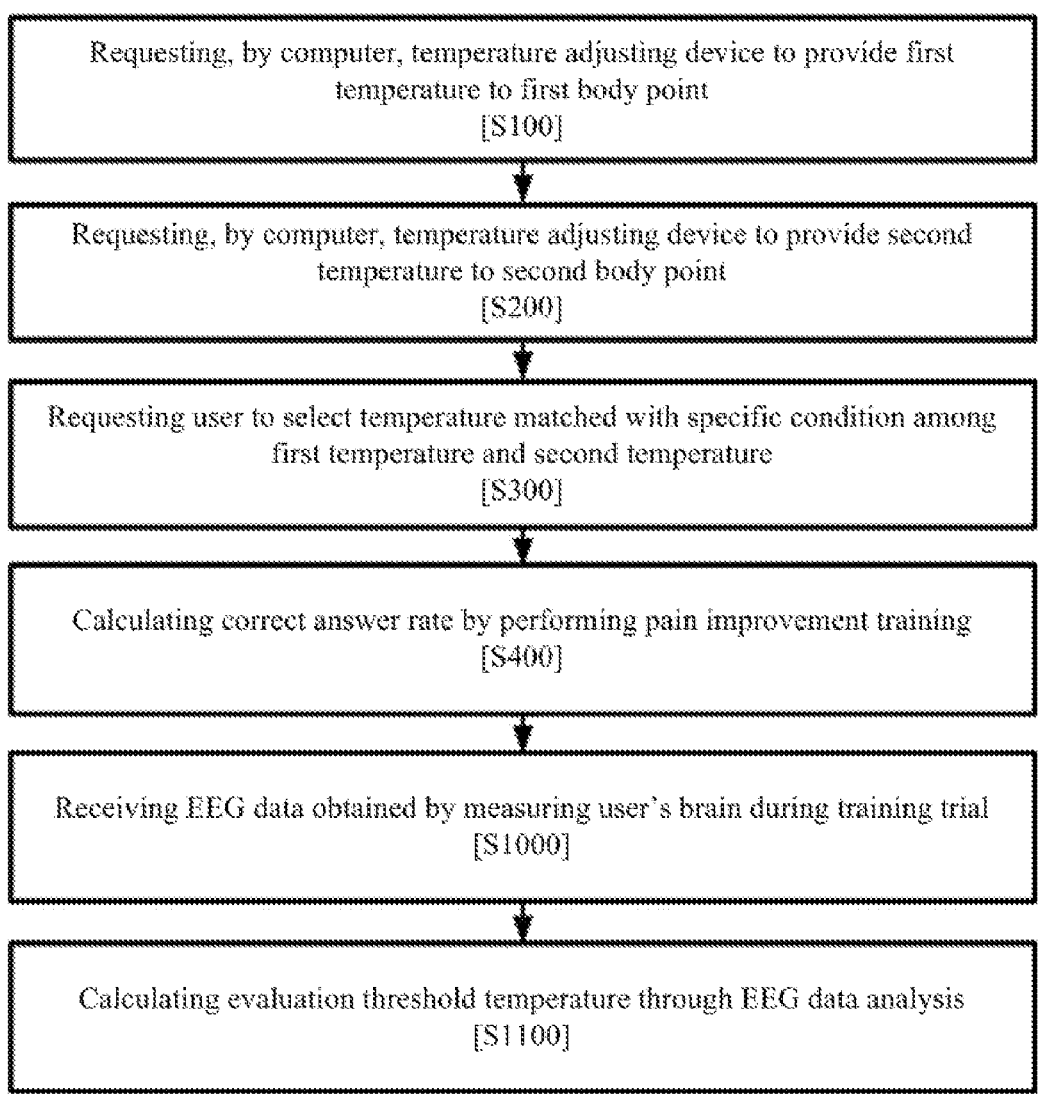

In addition, in another embodiment, as illustrated in FIG. 8, the method further includes an operation S1000 of receiving electroencephalography (EEG) data obtained by measuring the user's brain during the training trial and an operation S1100 of calculating the evaluation threshold temperature through the EEG data analysis. In S1000, the control device 100 obtains EEG data for the brain of the user (i.e., patient) by an EEG measurement device (not illustrated) (e.g., an EEG device). In S1100, the control device 100 calculates the evaluation threshold temperature by determining whether the user's brain recognizes that the first temperature or the second temperature is the pain, through the EEG data obtained at the same time as at a point in time when the first temperature and the second temperature are provided. The EEG measurement device may be a wearable device wearable on the user's head.

In particular, the control device 100 calculates the evaluation threshold temperature through the pain induction potential in the EEG data obtained by the EEG measurement device. When pain stimulus is repeatedly provided to a person at a high frequency, EEG (i.e., normal-state pain-induced potential; an EEG signal in response to repetitive pain stimulus) having the frequency of pain stimulus is induced. For the purpose of calculating the pain threshold (i.e. evaluation threshold temperature), the control device 100 requests the temperature providing device 200 to repeatedly provide pain pulses of various frequencies while changing temperature, and observes normal-state pain-induced potential using EEG. The control device 100 finds the temperature at which the pain-induced potential well occurs in the patient based on the magnitude of the pain-induced potential observed in normal persons depending on the intensity of the pain stimulus to calculate the optimized evaluation threshold temperature.

Moreover, in another embodiment, the evaluation threshold temperature may be calculated through analyzing brain image data obtained through medical imaging device. That is, the control device 100 obtains brain image data obtained by capturing the brain of a user (i.e., a patient) by an imaging device (not illustrated) (e.g., an MRI device). For example, the imaging device may correspond to a functional magnetic resonance imaging (fMRI) device that measures the change in blood oxygen level of the active part of the brain of the subject during measurement of the visual perception level of the subject. The control device 100 calculates the evaluation threshold temperature by determining whether the user's brain recognizes that the first temperature or the second temperature is the pain, through the brain image data captured at the same time as at a point in time when the first temperature and the second temperature are provided. Furthermore, in another embodiment, the method further includes setting, by the control device 100, reference image data. The reference image data is generated and received by the control device 100 or an external server based on brain image data while a normal person performs pain training.

The training method for pain improvement according to an embodiment of the inventive concept may be applied to a variety of users (i.e., patients). Embodiments of the inventive concept may be applied to chronic pain patients, patients suffering from diseases (e.g., cancer patients, diabetes patients, bone/joint disease patients), and the like. As the inventive concept is performed, users may obtain the effect of alleviating or relieving pain.

As a specific example, it is possible to relieve paresthesia, muscle weakness, and loss of balance, which are caused by peripheral neuropathy caused by side effects of anticancer drugs in cancer patients. Furthermore, for example, it may be used to treat abnormalities and pain, which are caused by diabetic foot due to the complication of diabetes. In the case of diabetic foot, the dull sensation may become sensitive by repeating the process of distinguishing temperature; accordingly, this may reduce the case wounds are severe or the foot needs to be cut because the patient won't be able to perceive the damage in the case where the foot is injured.

Also, it may restore general sensory nerves such as the senses of pain and heat associated with pain. That is, because paresthesia or loss of sensation (in particular, the loss of heat or pain) as one of the side effects of stroke is a great threat to survival, the temperature discrimination training may restore the sense of heat or pain.

As the training providing method according to embodiments of the inventive concept for pain improvement is performed, the pain may be improved when pain occurs without specific trauma to the specific body. In particular, as the training of distinguishing different temperature stimulus is performed repeatedly, it may reduce or treat chronic pain by increasing the threshold lowered due to brain abnormalities. Moreover, when the body may not distinguish the harmful stimulus well because brain damage, such as stroke, damages the nerves that perceive pain, the protective mechanism of the brain provides extreme pain signals even at the low temperature. Accordingly, it is possible to reduce pain by distinguishing non-hazardous stimulus by repeating the training that distinguishes the first and second temperatures to form new sensory cognitive representation of the first temperature and the second temperature.

The training providing method for pain improvement according to an embodiment of the inventive concept may be implemented by a program (or an application) and may be stored in a medium such that the program is executed in combination with the control device 100 being hardware. Hereinafter, the control device 100 is referred to as a "computer".

The program may include a code encoded using a computer language such as C, C++, JAVA, a machine language, or the like, which a processor (CPU) of the computer 100 can read through the device interface of the computer 100, such that the computer 100 reads the program and performs the methods implemented with the program. The code may include a functional codes associated with the function that defines functions necessary to perform the methods, and may include a control code associated with an execution procedure necessary for the processor of the computer 100 to perform the functions in a predetermined procedure. Furthermore, the code may further include additional information necessary for the processor of the computer 100 to perform the functions or a memory reference-related code associated with the location (address) of the internal or external memory of the computer 100, at which the media needs to be checked. Moreover, when the processor of the computer 100 needs to communicate with any other remote computer or any other remote server to perform the functions, the code may further include a communication-related code associated with how to communicate with any other remote computer or server using the communication module of the computer 100, what information or media should be transmitted or received during communication, or the like.

The stored media may mean the media that does not store data for a short period of time such as a register, a cache, a memory, or the like but semi-permanently stores to be read by the device. Specifically, for example, the stored media include, but are not limited to, ROM, RAM, CD-ROM, magnetic tape, floppy disk, optical data storage device, and the like. That is, the program may be stored in various recording media on various servers that the computer 100 can access, or various recording media on the computer 100 of the user. In addition, the media may be distributed to a computer system connected to a network, and the code readable by the computer 100 may be stored in a distribution manner.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, it is possible to repeatedly provide different temperatures to a patient, using the fact that the senses of pain and heat are transmitted to a brain through the same path, thereby relieving the pain by distinguishing between the senses of pain and heat to eventually increase the patient's threshold for pain.

In particular, as the pain improvement training according to embodiments of the inventive concept is provided to a patient (i.e., chronic pain patient) having pain due to abnormalities in the brain without tissue damage, the threshold (i.e., pain threshold) that the patient's brain determines as pain may be increased. In this way, the pain caused by the stimulation of low intensity may be relieved or eliminated.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A training providing computing device for pain improvement, the device comprising:
   at least one processor; and at least one memory communicatively connected to the at least one processor,
   wherein the at least one processor is configured to:
   request a temperature providing device to provide a first temperature to a first body point; request the temperature providing device to provide a second temperature to a second body point;
   request a user to select a temperature matched with a specific condition, among the first temperature and the second temperature; and
   calculate a correct answer rate after performing a trial of distinguishing between the first temperature and the second temperature by a predetermined number,
   wherein the control device is further configured to provide identification information, which includes at least one of visual information on a screen and auditory information from a speaker, to the user at a first point in time when the first temperature is provided and at a second point in time when the second temperature is provided, and
   wherein the at least one processor is further configured to adjust both the first temperature and the second temperature by an interval value based on the correct answer rate.

2. The device of claim 1, wherein the at least one processor is further configured to:
   when the correct answer rate is not greater than a reference condition, repeatedly provide a training of distinguishing between the first temperature and the second temperature of the same condition.

3. The device of claim 1, wherein the at least one processor is further configured to:
   make a request for providing the second temperature to the second body point distinct from the first body point, at the same time as providing the first temperature to the first body point.

4. The device of claim 1, wherein the at least one processor is further configured to:
   set the first body point and the second body point to the same body point to sequentially provide the first temperature and the second temperature while changing an order of the first temperature and the second temperature for each training trial.

5. The device of claim 1, wherein the at least one processor is further configured to
set the first temperature to the same temperature as an expected threshold temperature or a temperature lower than the expected threshold temperature by a first value, and
set the second temperature to a temperature higher than the expected threshold temperature by a second value.

6. The device of claim 5, wherein the at least one processor is further configured to adjust the first temperature and the second temperature based on the correct answer rate, and adjust the second value based on the expected threshold temperature.

7. A training providing system, the system comprising:
a computing device of claim 1; and
a temperature providing device configured to provide different temperatures simultaneously or continuously,
wherein the temperature providing device links with the computing device through wired or wireless communication so as to be controlled by the computing device.

8. The training providing system of claim 7, wherein the temperature providing device includes a first temperature transmitter configured to provide the first temperature and a second temperature transmitter configured to provide the second temperature, which is different from the first temperature,
the first body point and the second body point are the same point of a body of the user,
the first temperature transmitter is configured to move along with a first diagonal direction from a bottom surface of a temperature control module, to be positioned at the first body point at a time of providing the first temperature and to be replaced with the second temperature transmitter at a time of providing the second temperature, and
the second temperature transmitter is configured to move along with a second diagonal direction from the bottom surface of the temperature control module, to be positioned at the first body point at the time of providing the second temperature and to be replaced with the first temperature transmitter at the time of providing the first temperature.

9. A non-transitory computer-readable recording medium storing a training providing computer program for pain improvement, to be executed by a processor of a computer, the program including instructions for
requesting a temperature providing device to provide a first temperature to a first body point;
requesting the temperature providing device to provide a second temperature to a second body point;
providing identification information, which includes at least one of visual information on a screen and auditory information from a speaker, to a user at a first point in time when the first temperature is provided and at a second point in time when the second temperature is provided;
requesting the user to select a temperature matched with a specific condition, among the first temperature and the second temperature;
calculating a correct answer rate after performing a trial of distinguishing between the first temperature and the second temperature by a predetermined number,
providing identification information, which includes at least one of visual information on a screen and auditory information from a speaker, to the user at a first point in time when the first temperature is provided and at a second point in time when the second temperature is provided; and
adjusting both the first temperature and the second temperature by an interval value based on the correct answer rate.

10. A training providing computing device for pain improvement, the device comprising:
at least one processor; and
at least one memory communicatively connected to the at least one processor,
wherein the at least one processor is configured to:
request a temperature providing device to provide a first temperature to a first body point;
request the temperature providing device to provide a second temperature to a second body point;
request a user to select a temperature matched with a specific condition, among the first temperature and the second temperature; and
calculate a correct answer rate after performing a trial of distinguishing between the first temperature and the second temperature by a predetermined number,
wherein the control device is further configured to provide identification information, which includes at least one of visual information on a screen and auditory information from a speaker, to the user at a first point in time when the first temperature is provided and at a second point in time when the second temperature is provided,
wherein the at least one processor is further configured to repeatedly increase or decrease the first temperature and the second temperature with an interval value after performing training of a specific number of trials, and
wherein the at least one processor is further configured to determine whether a correct answer rate is greater than a threshold value, and increase the interval value when it is determined that the correct answer rate is greater than the threshold value.

* * * * *